United States Patent [19]

Levy et al.

[11] Patent Number: 4,816,249

[45] Date of Patent: Mar. 28, 1989

[54] MONOCLONAL ANTI-IDIOTYPE ANTIBODIES

[75] Inventors: Ronald Levy, Stanford; Jeanette Dilley; David G. Maloney, both of Mt. View; Richard A. Miller, Palo Alto, all of Calif.

[73] Assignee: The Board of Trustees of the Leland Stanford Junior University, Palo Alto, Calif.

[21] Appl. No.: 16,281

[22] Filed: Feb. 19, 1987

Related U.S. Application Data

[60] Division of Ser. No. 557,655, Dec. 2, 1983, Pat. No. 4,661,586, which is a continuation-in-part of Ser. No. 322,377, Nov. 17, 1981, abandoned.

[51] Int. Cl.4 .................................. A61K 39/395
[52] U.S. Cl. ................................ 424/85.8; 530/387; 435/240.27; 435/7; 424/86; 436/548
[58] Field of Search .............. 424/85; 530/387; 514/8, 514/21

[56] References Cited

U.S. PATENT DOCUMENTS 4,172,124 10/1979 Koprowski .
4,513,088 4/1985 Levy et al. .................... 436/518

OTHER PUBLICATIONS

Hamblin et al, *Chem Abs*, 94(11):76974g, 1980.
Krolick et al, Imm Rev, 48, 81–106, 1979.
Haughten et al, J. Immunol., 121(6), Dec. 1978.
Sevier et al, Clin. Chem., 27(11), 1797–1806, 1981.
Kohler et al., (1975), Nature, 256: 495–497.
Levy et al., in *Monoclonal Antibodies*, (Kennet et al., eds. Plenum Press, 1980), pp. 137–153.
Brown et al., (1980), J. Immunol., 125:1037–1043.
Littlefield, (1964), Science, 145:709–710.
Stevenson et al., (1977), Fed. Proc., 36:2268–2271.
Stevenson et al., (1975), Nature, 254:714–716.
Hough et al., (1976), J. Exp. Med., 144:960–969.
Levy et al., (1978), Proc. Natl. Acad. Sci. (USA), 75(5):2411–2415.
Kennet et al., in *Methods in Enzymology* (Academic Press, N.Y. 1979), pp. 345–359.
Mayumi et al., (1982), J Immunol., 129(2):904–910.
Hamblin et al., (1980), Br. J. Cancer, 42:495–502.
Hatzubai et al., (1981), J. Immunol., 126(6):2397–2402.
Thorpe et al., (1978), Nature, 271:752–755.
Gerhard et al., (1981), Proc. Natl. Acad. Sci., 78(5):3225–3229.

*Primary Examiner*—Howard E. Schain
*Assistant Examiner*—Jeff P. Kushan
*Attorney, Agent, or Firm*—Ciotti & Murashige, Irell & Manella

[57] ABSTRACT

Monoclonal anti-idiotype antibodies against cell surface Ig of human B-cell tumors, labeled conjugates of such antibodies, immunotherapeutic compositions containing such antibodies, and a process for making such antibodies. The nodular lymphoma of a patient treated with a monoclonal anti-idiotype antibody against the cell surface IgM of the patient's tumor went into complete remission.

4 Claims, No Drawings

MONOCLONAL ANTI-IDIOTYPE ANTIBODIES

CROSS-REFERENCE TO RELATED APPLICATION

This application is a division of application Ser. No. 557,655, filed Dec. 2, 1983, now U.S. Pat. No. 4,661,586, which is a continuation-in-part of Ser. No. 322,377, filed Nov. 17, 1981, now abandoned.

REFERENCE TO GRANTS

This invention was supported by Grant No. 21223 awarded by National Institute of Health and Grant No. IM 114B awarded by the American Cancer Society.

TECHNICAL FIELD

The invention is in the field of immunology and relates particularly to monoclonal antibodies.

BACKGROUND ART

Somatic cell hybridization techniques to produce monoclonal antibodies of defined class, avidity, and specificity were first developed by Kohler, G. and Milstein, C., Nature, 256: 495–497 (1975). Briefly, the technique involves fusing myeloma cells and lymphocytes using a fusogen such as polyethylene glycol. The fused cells or hybridomas are then expanded in a nutrient medium and then selected by incubation in a selective medium such as HAT medium. The cells surviving the incubation are assayed for production of the desired antibody and positive hybrids are sorted and cloned. The monoclonal antibodies produced by the clones may be harvested and purified.

U.S. Pat. No. 4,172,124 uses the above described method to make hybridomas that produce monoclonal antibodies against human tumor cells. The patent specifically describes the preparation of monoclonal antibodies against human melanoma cells and human colorectal carcinoma cells by hybridizing mouse myeloma cells to spleen cells from mice immunized with such tumor cells.

Heterologous anti-idiotype antibodies against human B-cell tumors have been prepared and studied by Levy, R. et al. Monoclonal Antibodies, Plenum Press, Ed by Kennet, et al, 1980, pp 137–153. Brown, S. et al, J. Immun. (1980) 125: 1037–1043 also describe such antibodies. These antibodies were prepared by hybridizing non-Ig secreting human B-leukemia cells to mouse myeloma cells to produce human Ig secreting hybridomas. The human Ig secreted by the fused cells was used as an immunogen to immunize rabbits which produced anti-idiotype antibodies against the surface Ig of the tumor cells. Hough, et al, J. Exp. Med., 1976, 144: 960 also made heterologous anti-idiotype antibodies against human B-cell tumors using Fab$\mu$ fragments released from tumor cell surfaces by limited papain digestion as an immunogen.

DISCLOSURE OF THE INVENTION

One aspect of the invention is novel monoclonal anti-idiotype antibodies against surface Ig of human B-cell tumors. These antibodies have been found to be remarkably effective immunotherapeutic agents. These antibodies are also useful as immunodiagnostic agents.

A second aspect of the invention is novel conjugates of such monoclonal anti-idiotype antibodies and an immunotoxin.

A third aspect of the invention is a novel immunotherapeutic composition comprising such monoclonal anti-idiotype antibodies of the IgG class combined with a pharmaceutically acceptable vehicle.

Yet another aspect is a process for making monoclonal anti-idiotype antibodies against surface Ig of a substantially non Ig-secreting human B-cell tumor comprising:

(a) hybridizing cells of said B-cell tumor to myeloma cells to produce hybridomas that secrete said Ig;

(b) immunizing a host with Ig secreted by the hybridomas;

(c) hybridizing cells from the immunized host that produce antibodies against said Ig with myeloma cells to produce hybridomas that secrete anti-idiotype antibodies against said surface Ig;

(d) cloning the hybridomas of step (c); and (e) harvesting said monoclonal anti-idiotype antibodies from the clones.

MODES FOR CARRYING OUT THE INVENTION

About 80% of adult lymphoproliferative malignancies involve Ig containing or Ig producing tumors. These tumors, called B-cell tumors, include those associated with leukemias and lymphomas such as chronic lymphocytic leukemia, lymphosarcoma-cell leukemia, nodular lymphoma, large-cell lymphoma, Burkitt's lymphomas, hairy-cell leukemia, "undifferentiated" lymphoma, and acute lymphocytic leukemia of pre-B-cell type. The tumor cell populations of these cancers are clonal in nature and appear to contain cells arrested in various stages of differentiation with respect to Ig synthesis and secretion. Because the tumor population is monoclonal, the Ig produced by the population is likewise monoclonal. That is, the Ig that is expressed or secreted is restricted to a single $V_H$ and $V_L$ region and to a single light chain of either the $\kappa$ or $\lambda$ type. Although some of these malignancies secrete large amounts of Ig, in most of them the Ig is inserted or anchored in the tumor cell membrane by the $F_c$ portion of the Ig molecule and there is little or no active secretion by the tumor cells. The invention is directed to monoclonal anti-idiotype antibodies against the surface Ig of these latter, substantially non Ig secreting human B-cell tumors.

The first step in the process is to obtain the immunogen (i.e., the Ig from the patient's tumor cells). This immunogen may be prepared in several ways. One procedure involves "rescuing" secretion of monoclonal Ig from the nonsecreting tumor cells. The "rescuing" technique is disclosed by Levy, R. et al, (1978) PNAS USA 75: 2411, and by Brown, S. et al, (1980) J. Immunol., 125: 1037, which disclosures are incorporated herein by reference. In it, the tumor cells are hybridized to myeloma cells. The tumor cells are isolated from a peripheral blood sample taken from the patient or from a biopsy specimen and fused with a myeloma cell line that fuses efficiently and will support high-level synthesis and secretion of Ig by its hybridized tumor cell partner. While myeloma cells from any species may be used, murine myeloma lines having the above characteristics are available currently and are therefore preferred. Examples of such lines are those derived from the original MOPC-21 or MPC-11 mouse tumors. The particular murine myeloma lines that have been effectively fused with nonsecreting human B-cell tumors to date are the P3/X63-Ag8 and NS1-Ag4 lines (available from the Salk Institute, Cell Distribution Center, P.O. Box 1809, San Diego, Calif. 92112). The fusion is carried out in the presence of a fusogen, such as polyethylene glycol having a molecular weight of about 1000 to 6000 daltons, using a myeloma cell:B-cell tumor ratio of about 1:1. Cell ratios other than 1:1 may be used, but best results are obtained at a 1:1 ratio. The individual cell concentrations will typically be in the range of about $10^6$ to $10^8$, preferably $1-5 \times 10^7$ cells/ml. After the fusion, the cells are washed to remove fusogen and are then seeded in a selective medium, such as HAT medium (Littlefield (1964) *Science*, 145, 709–710), to eliminate free myeloma cells and leave HAT resistant hybrids. Culturing in the selective medium will normally take about 4 to 8 weeks.

Ig-secreting hybrids are identified by immunoassay. The idiotypical identity of the Ig secreted by them with the cell surface Ig of the B-cell tumor is determined by immunoassay or other means. Positive cells are cloned and the resulting clones are expanded in an appropriate cell culture medium. The Ig secreted by the clones may be isolated from the culture medium by known techniques such as ammonium sulfate precipitation followed by affinity chromatography on an anti-human $\mu$ chain column. This immunoglobulin is usually of the IgM class ($\mu$ heavy chain) and has a homogenous $\kappa$ or $\lambda$ light chain. The heavy and light chains are typically combined as full homogenous IgM pentamers. The $\mu$ chain mobility of this IgM is substantially identical to the $\mu$ chain mobility of the cell surface (membrane) IgM of the original tumor cells.

The next step in the manufacture of the monoclonal anti-idiotype antibodies is to immunize a host animal with the IgM secreted by the above-described hybridomas. Alternatively, the B-cell tumor and murine myeloma hybridomas may be used directly as an immunogen for immunizing the host to produce anti-idiotype Ig-producing fusing partners. Another alternative and preferred procedure is to use the patient's B-cell tumors directly as an immunogen rather than the B-cell tumor $\times$ murine myeloma hybridomas. This preferred procedure is described by Mayumi, M. et al, *J. Immun.* (1982) 129: 904–910 which disclosure is incorporated by reference. Mice are commonly used as the host. The host is usually immunized with at least about 100 $\mu$g per injection of the isolated IgM (or at least about $10^5$, more usually $10^5$ to $10^8$ hybridoma cells or the patient's tumor cells) at least twice with the booster coming about one week after the initial inoculation. Three days after the last boost, spleen cells or other antibody-producing cells are taken from the host.

The spleen cells taken from the immunized host are fused with an appropriate myeloma cell line using the somatic cell hybridization techniques described above. The same myeloma cell lines, fusogen, fusion conditions and hybridoma expansion, selection and cloning procedures that are used in preparing the myeloma $\times$ B-cell tumor hybridomas may be used to prepare these spleen cell $\times$ myeloma cell hybrids. The resulting clones may be examined for production of anti-idiotype antibody against the secreted IgM (and thus against the tumor membrane IgM) by immunoassay. A preferred assay procedure is described in commonly owned, copending application Ser. No. 06/480,478 filed Mar. 30, 1983 entitled "Assay for Monoclonal Antibody Against Surface Ig of a Human B-Cell Tumor". The disclosure of that application is incorporated herein by reference. Monoclonal anti-idiotype antibodies of the IgG class are preferred because available evidence indicates they are effective in immunotherapy. The particular IgG subclass does not appear to be critical and antibodies of IgG subclasses 1, 2a, and 2b have been produced and used. Antibodies of other classes (IgM, IgE, and IgD) may also prove to be useful in immunotherapy, however, available evidence suggests that antibody of the IgM class is relatively ineffective as an immunotherapeutic agent. Clones secreting such monoclonal anti-idiotype antibodies may be subcloned under limiting dilution conditions. The antibodies may be separated from the culture medium by known techniques such as ammonium sulfate precipitation, DEAE cellulose chromatography, or affinity chromatography. Further purification of the antibodies, if desired, may be achieved by ultracentrifugation and microfiltration.

An alternative process for preparing these monoclonal anti-idiotype antibodies is to use Fab fragments of the cell surface Ig of the tumors as an immunogen with which to prime the host animal. These Fab $\mu$ fragments are released from the tumor cell surfaces by limited papain digestion as described in Hough, et al, supra and Stevenson, et al, (1977) *Fed. Proc.* 36: 2268 and (1975) *Nature* 254: 714. Also, it may become possible in the future to produce these antibodies in other cells or microorganisms by removing the anti-idiotype antibody genes from the spleen cell $\times$ myeloma cell hybridomas and transferring them to such cells or microorganisms.

The monoclonal anti-idiotype antibodies of the invention may be used in immunodiagnosis and/or immunotherapy (antibodies of the IgM class, as indicated previously, are relatively ineffective immunotherapeutic agents). In this regard, the antibodies of the invention are specific only to the cell surface Ig of the tumor from which they were derived and cannot be used in the diagnosis or treatment of other patients. In other words, each patient will require his or her own unique monoclonal anti-idiotype antibody. When used in immunodiagnosis to monitor the therapy or remission status of the patient these antibodies may be conjugated with labels such as the well known radiolabels, fluorescent labels or enzyme labels or they may be used without labels. These monoclonal anti-idiotype antibodies can be used to test blood samples taken from the patient for the presence of tumor cells or free idiotype protein secreted from the tumor cells. In this regard the percentage of idiotype IgM positive cells in the patient's total circulating mononuclear cell population and the concentration of circulating idiotype IgM in the serum both have been found to correlate to the patient's clinical status. Alternatively, it may be possible to administer labeled anti-idiotype antibodies to the patient. The rate of disappearance of the anti-idiotype will then correlate with the amount of tumor cells present.

When used in immunotherapy the antibodies are administered to the patient in a manner and dose that induce a B-cell tumor elimination response. They will normally be administered parenterally, preferably intravenously, at a dose in the range of 10 mg to 5 g, usually 100 to 400 mg. In most instances the elimination mechanism induced by the antibodies will involve coating of the tumor cells by the antibodies (opsonization) followed by antibody-dependent cell mediated cytotoxicity (ADCC). ADCC involves reaction of the antibody coated tumor cells with effector cells of the monocyte lineage, called killer (K) cells, causing contact lysis rather than phagocytosis. It is also possible to conjugate the antibodies with toxins such as ricin and $^{131}$I using the same basic procedures as are used to bind labels to the antibodies. The administration of conjugates of the antibodies and such cytoxic agents may cause tumor cell destruction by other mechanisms. In any event, the affected tumor cells and/or tumor cell destruction products are removed by the patient's reticuloendothelial system. A preferred immunotherapeutic regimen for treating human B-cell malignancies with these monoclonal antibodies is described and claimed in commonly owned U.S. patent application Ser. No. 315,896 filed Oct. 28, 1981 entitled "Immunotherapeutic Method for Treating Cancer", now abandoned. The disclosure of that application is incorporated herein by reference. Briefly, that regimen involves administering the antibody at a time when the patient's serum is substantially free, i.e., contains below 100 $\mu$g/ml, of circulating idiotype IgM and readministering the antibody after the serum returns to a substantially circulating idiotype IgM-free condition, antigenic modulation, if any, of the tumor cells reverses, and the patient's reticuloendothelial system recovers such that it is able to effectively remove affected tumor cells and/or tumor cell destruction debris. This administration sequence is repeated until the patient's tumor burden is in at least partial remission, preferably in complete remission.

For parenteral administration the antibodies will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and Hank's solution. Nonaqueous vehicles such as fixed oils and ethyl oleate may also be used. A preferred vehicle is 5 w% human albumin in saline. The vehicle may contain minor amounts of additives such as substances that enhance isotonicity and chemical stability, e.g., buffers and preservatives. The antibody is typically formulated in such vehicles at concentrations of about 1 $\mu$g/ml to 10 mg/ml.

The following example describes the preparation of a monoclonal anti-idiotype antibody against the surface IgM of a human B-cell malignancy, and the use of that antibody to monitor and treat a patient's malignancy. The following abbreviations are used in this example: Ka, a patient with nodular lymphoma; Id, idiotype; RIA, radioimmunoassay; PBS, 0.14M NaCl-0.02M NaHPO$_4$$_P$, pH 7.4: DMSO, dimethylsulfoxide; BSA, bovine serum albumin; PBL, peripheral blood lymphocytes; FACS, fetal calf serum.

PREPARATION OF ANTIBODY: MATERIALS AND METHODS

Human malignant cells. Malignant lymphocytes from a patient (Ka) with nodular lymphoma were isolated from the peripheral blood and stored as described in Brown, et al, supra.

Preparation of Ka Id-bearing Ig. PBL from patient Ka were fused with the mouse myeloma line NS1/Ag4 as described in Brown, et al, supra, and Levy, et al, supra. Clones resulting from this hybridization secreted human IgM$\lambda$ that was idiotypically identical to the IgM found in the membrane of Ka's malignant cells. Clone K6H6, having lost production of the murine NS-1 light chain, secreted only the human IgM$\lambda$. This Ig(Id$^{Ka}$-Ig) was isolated from K6 H6 culture fluids by affinity chromatography, on a Sepharose-linked goat anti-human IgM column as described in Brown, et al, supra.

Monoclonal antibodies. A Balb/C mouse was immunized with Id$^{Ka}$-Ig (100 $\mu$g) in complete Freund's adjuvant i.p. at day 0. At day 7 the mouse was boosted with 100 $\mu$g Id$^{Ka}$-Ig in PBS i.v. The mouse spleen was removed at day 10. The spleen cells were fused with P3/X63/Ag8.653 cells according to Kennet's fusion protocol (Kennet, et al, (1979) *Cell Fusion. In Methods in Enymology.* Academic Press, New York, pp. 345–357).

Clones were examined for secretion of antibodies specific for human $\mu$- or $\lambda$-chain and for Id$^{Ka}$ by RIA. One clone, identified as DM11, was found to produce an IgM with anti-Id$^{Ka}$ antibody activity. Another clone, identified as 4D6 was found to produce an IgG2b with anti-Id$^{Ka}$ antibody activity. Subcloning of clones secreting these antibodies was performed by limiting dilutions into wells containing normal mouse spleen cells as feeders.

Purification of monoclonal anti-Id antibody. Immunoabsorption on an Id$^{Ka}$ Sepharose column of 40 ml of the culture medium of DM11 yielded 2.5 mg of pure anti-Id$^{Ka}$ antibody of the IgM class. The antibody was eluted with 6M quanidine hydrochloride.

Large quantities of 4D6 were obtained from malignant ascites produced by the intraperitoneal injection of the hybridoma cells into Pristane-primed Balb/C mice. The antibody was purified from the ascites by ammonium sulfate precipitation, dialized against 0.9% NaCl and ultracentrifuged to remove lipid and aggregate.

Specificity of monoclonal anti-Id$^{Ka}$ antibody. An RIA was used in which plates were coated with Id$^{Ka}$ Ig and seven other human IgM samples. The binding of the antibody to the Ig on the plates was detected with radioiodinated goat anti-mouse $\kappa$. The anti-idiotype antibody reacted with the Id$^{Ka}$Ig but did not react with any of the other seven IgM.

Radioimmunoassay: RIA to test for specificity of monoclonal antibodies to human $\mu$- or $\kappa$-chain and Id$^{Ka}$. A solid phase RIA was performed by using polyvinyl microtiter plates (Cooke Laboratory Products) coated by absorption with various human Ig at a concentration of 10 $\mu$g/ml. After coating, the plates were washed with PBS-5% FCS. To the coated wells, 25 $\mu$l of test culture samples were added. The plates were then incubated overnight at 4° C. and washed 4 times with PBS-5% FCS, after which $^{125}$I-labeled goat anti-mouse $\kappa$ was added. The plates were incubated for at least another 4 hr and washed. The wells were cut out with a hot wire device and counted in a gamma counter.

USE OF ANTIBODY TO MONITOR MALIGNANCY

The immunofluorescent staining technique used in this monitoring was as follows:

Reagents. Biotinylated IgM antibody was prepared by modification of the method described by Heitzmann and Richards (1975) *PNAS* 71: 3537. Partially purified antibodies at a concentration of 0.5 to 1 mg/ml were dialyzed against 0.1M NaHCO$_3$, pH 8.6. Biotin succinimide ester (Biosearch, San Rafael, CA) was dissolved in DMSO just before use at 1.0 mg/ml. To a 1-ml protein solution, 120 $\mu$l of biotin ester solution was added, and these were mixed and left at room temperature for 4 hr. The biotinylated antibody was dialyzed against PBS with 0.02% sodium azide overnight. Rhodamine-avidin and fluorescein-avidin were from Vector Laboratories, Burlingame, CA.

Method. PBL isolated by Ficoll (Pharmacia Fine Chemicals) Hypaque (Winthrop Laboratories, New York) sedimentation (Boyum (1968) *Scand. J. Clin. Lab.*

*Invest.* 21: 77) were washed with PBS, resuspended in RPMI 1640 medium containing 15% FCS, and cultured overnight at 37° C. in 5% $CO_2$ to remove cytophilic Ig. Cells stored in liquid $N_2$ were washed in RPMI 1640, and live cells were separated by Ficoll-Hypaque sedimentation. Cells were then suspended in 2% BSA, 0.02% sodium azide, at a concentration of $2\times10^7$/ml and 0.1 ml were incubated with an equal volume of biotinylated antibody for 20 min at room temperature. Cells were then washed twice with the BSA-azide solution and were incubated in a similar manner with the 2nd stage reagent, either rhodamine-avidin or fluorescein-avidin. After washing as above, the cells were layered on glass slides, covered with glass coverslips, and sealed with nail polish for viewing with a fluorescence microscope. Alternatively, the stained cells were fixed in 1% formaldehyde in PBS and analyzed on the FACS within 48 hr.

The monoclonal anti-Id$^{Ka}$ was used to stain PBL isolated from patient Ka and from 4 normal donors. Biotinylated monoclonal anti-Id$^{Ka}$ was used as a 1st stage, with rhodamine or fluorescein-avidin as the 2nd stage. PBL isolated from normal donors did not stain with the monoclonal anti-Id$^{Ka}$ antibody, whereas the percentage of Ka PBL stained correlated with the patient's clinical condition. The percentage of Id$^{Ka}+$ cells varied from a high of 75% of total mononuclear cells, taken when the disease was rapidly progressing clinically, to a low of 1% to 3% when the disease was in partial remission after chemotherapy.

Moreover, the patient's serum was analyzed for the amount of free circulating Id$^{Ka}$-Ig. The concentration of this protein was defined by RIA using a standard solution of purified Id$^{Ka}$-Ig as reference. The concentration of circulating Id$^{Ka}$-Ig in the patient's sera correlated well with the number of Id$^{Ka}+$ cells and with the patient's clinical condition. The lowest concentration of Id$^{Ka}$-Ig was found during apparent remissions, and the highest concentrations occurred when the disease was most active and apparent clinically.

USE OF THE ANTIBODY TO TREAT MALIGNANCY

Immunofluorescence Staining. For direct immunofluorescence staining, $1\times10^6$ cells were incubated with 100 μl (1 mg) of fluoresceinated antibodies for 20–30 minutes at 4° C. Indirect staining was performed in a similar manner using unlabeled first stage antibody. After washing, 100 μl of fluoresceinated goat anti-mouse IgG was added to the cells for 20–30 minutes at 4° C. Immunofluorescence staining of cells was analyzed using a FACS.

Frozen section immunoperoxidase staining of Ka tissue using the antibody was also performed.

Administration of Anti-Idiotype. The purified 4D6 antibody was given as a continuous six-hour infusion in 250 cc of normal saline containing 5% human albumin (400 mg antibody). Prior to each infusion the patient was given acetaminophen and diphenhydramine.

Assessment of Clinical Response. During the period of monoclonal antibody therapy, frequent complete blood counts, platelet counts, creatinine, electrolyte studies and hepatic and renal function tests were performed. Palpable cervicle, inguinal and axillary lymphadenopathy and hepatosplenomegaly were followed by physical examination. Abdominal roentgenograms were obtained to evaluate changes in opacified para-aortic and iliac lymphadenopthy seen on lymphangiogram.

Changes in tumor burden were estimated by measuring lymph node size on serially obtained abdominal films. Three lymph nodes on each side of the vertebral column, and one lymph node in the center, were used to calculate tumor volume by multiplying the larger diameter by the square of the smaller diameter of each lymph node. The sum of the volumes of these lymph nodes was then normalized to the value of the pre-treatment lymph node volume and was designated the tumor volume index.

Effect of Administration of Anti-Idiotype on Serum Idiotype Level. We anticipated that free circulating idiotype protein would be an obstacle to in vivo therapy with anti-idiotype. Moreover, the formation of immune complexes between idiotype and anti-idiotype might have been toxic. Since plasmapheresis was not able to reduce the idiotype level, the 4D6 antibody was given slowly on an intermittant schedule beginning with a low dose. Serum idiotype levels were unaffected by 1 or 5 mg of anti-idiotype but 15 mg caused a dramatic fall in idiotype level. Over the next five days, serum idiotype returned to approximtely two-thirds of the pre-treatment level. No toxicity was apparent and the patient experienced no side effects. Anti-idiotype was then administered in higher doses. Forty mg and 75 mg doses caused progressively greater decreases in serum idiotype. After 75 mg, idiotype dropped to undetectable levels for a short time but had reappeared just prior to a 150 mg dose. Subsequent to the 150 mg dose, idiotype was no longer detectable.

Detection of Monoclonal Anti-Idiotype in Serum During In Vivo Therapy. As would be expected, the detectability of anti-idiotype correlated with the disappearance of serum idiotype. After the 15 mg dose, circulating murine immunoglobulin was barely detectable and disappeared when idiotype levels rose. With the subsequent higher doses, serum anti-idiotype levels progressively rose with sharp increases seen after each dose. Serum anti-idiotype was detectable for over three weeks after the last doses of antibody. The serum levels of anti-idiotype were dose related as the bioavailability was greater for 150 mg>135 mg>85 mg. This relationship also depended on the absence of free idiotype.

Detection of 4D6 Anti-Idiotype in Lymph Node. After five doses of anti-idiotype, no measurable tumor response had been noted despite reduction in idiotype levels and appearance of circulating anti-idiotype. Despite these measurements it was important to determine if anti-idiotype could reach tissue sites such as lymph nodes. A repeat left cervical lymph node biopsy was performed two hours following the 150 mg dose of antibody. A cell suspension of this lymph node was stained with fluorescein-conjugated goat anti-mouse antibody to determine if murine antibody was present on the cells of the lymph node. Some murine antibody was present on the lymph node cells but these cells were not fully saturated since more intense staining could be obtained by incubation with additional 4D6 antibody in vivo. Thus, anti-idiotype was capable of penetrating and binding to cells within the lymph node, although the antigenic sites were not fully saturated at this time.

Tumor Response to anti-Idiotype Therapy. It should be emphasized that the patient received no therapy other than antibody during the period of this trial or in the preceding several weeks and that he had progressive tumor immediately prior to receiving the anti-idithe antibodies. The administration of conjugates of the antibodies and such cytoxic agents may cause tumor cell destruction by other mechanisms. In any event, the affected tumor cells and/or tumor cell destruction products are removed by the patient's reticuloendothelial system. A preferred immunotherapeutic regimen for treating human B-cell malignancies with these monoclonal antibodies is described and claimed in commonly owned U.S. patent application Ser. No. 315,896 filed Oct. 28, 1981 entitled "Immunotherapeutic Method for Treating Cancer", now abandoned. The disclosure of that application is incorporated herein by reference. Briefly, that regimen involves administering the antibody at a time when the patient's serum is substantially free, i.e., contains below 100 $\mu$g/ml, of circulating idiotype IgM and readministering the antibody after the serum returns to a substantially circulating idiotype IgM-free condition, antigenic modulation, if any, of the tumor cells reverses, and the patient's reticuloendothelial system recovers such that it is able to effectively remove affected tumor cells and/or tumor cell destruction debris. This administration sequence is repeated until the patient's tumor burden is in at least partial remission, preferably in complete remission.

For parenteral administration the antibodies will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and Hank's solution. Nonaqueous vehicles such as fixed oils and ethyl oleate may also be used. A preferred vehicle is 5 w% human albumin in saline. The vehicle may contain minor amounts of additives such as substances that enhance isotonicity and chemical stability, e.g., buffers and preservatives. The antibody is typically formulated in such vehicles at concentrations of about 1 $\mu$g/ml to 10 mg/ml.

The following example describes the preparation of a monoclonal anti-idiotype antibody against the surface IgM of a human B-cell malignancy, and the use of that antibody to monitor and treat a patient's malignancy. The following abbreviations are used in this example: Ka, a patient with nodular lymphoma; Id, idiotype; RIA, radioimmunoassay; PBS, 0.14M NaCl-0.02M NaHPO$_{4P}$, pH 7.4: DMSO, dimethylsulfoxide; BSA, bovine serum albumin; PBL, peripheral blood lymphocytes; FACS, fetal calf serum.

PREPARATION OF ANTIBODY: MATERIALS AND METHODS

Human malignant cells. Malignant lymphocytes from a patient (Ka) with nodular lymphoma were isolated from the peripheral blood and stored as described in Brown, et al, supra.

Preparation of Ka Id-bearing Ig. PBL from patient Ka were fused with the mouse myeloma line NS1/Ag4 as described in Brown, et al, supra, and Levy, et al, supra. Clones resulting from this hybridization secreted human IgM$\lambda$ that was idiotypically identical to the IgM found in the membrane of Ka's malignant cells. Clone K6H6, having lost production of the murine NS-1 light chain, secreted only the human IgM$\lambda$. This Ig(Id$^{Ka}$-Ig) was isolated from K6 H6 culture fluids by affinity chromatography, on a Sepharose-linked goat anti-human IgM column as described in Brown, et al, supra.

Monoclonal antibodies. A Balb/C mouse was immunized with Id$^{Ka}$-Ig (100 $\mu$g) in complete Freund's adjuvant i.p. at day 0. At day 7 the mouse was boosted with 100 $\mu$g Id$^{Ka}$-Ig in PBS i.v. The mouse spleen was removed at day 10. The spleen cells were fused with P3/X63/Ag8.653 cells according to Kennet's fusion protocol (Kennet, et al, (1979) *Cell Fusion. In Methods in Enymology.* Academic Press, New York, pp. 345–357).

Clones were examined for secretion of antibodies specific for human $\mu$- or $\lambda$-chain and for Id$^{Ka}$ by RIA. One clone, identified as DM11, was found to produce an IgM with anti-Id$^{Ka}$ antibody activity. Another clone, identified as 4D6 was found to produce an IgG2b with anti-Id$^{Ka}$ antibody activity. Subcloning of clones secreting these antibodies was performed by limiting dilutions into wells containing normal mouse spleen cells as feeders.

Purification of monoclonal anti-Id antibody. Immunoabsorption on an Id$^{Ka}$ Sepharose column of 40 ml of the culture medium of DM11 yielded 2.5 mg of pure anti-Id$^{Ka}$ antibody of the IgM class. The antibody was eluted with 6M quanidine hydrochloride.

Large quantities of 4D6 were obtained from malignant ascites produced by the intraperitoneal injection of the hybridoma cells into Pristane-primed Balb/C mice. The antibody was purified from the ascites by ammonium sulfate precipitation, dialized against 0.9% NaCl and ultracentrifuged to remove lipid and aggregate.

Specificity of monoclonal anti-Id$^{Ka}$ antibody. An RIA was used in which plates were coated with Id$^{Ka}$ Ig and seven other human IgM samples. The binding of the antibody to the Ig on the plates was detected with radioiodinated goat anti-mouse $\kappa$. The anti-idiotype antibody reacted with the Id$^{Ka}$Ig but did not react with any of the other seven IgM.

Radioimmunoassay: RIA to test for specificity of monoclonal antibodies to human $\mu$- or $\kappa$-chain and Id$^{Ka}$. A solid phase RIA was performed by using polyvinyl microtiter plates (Cooke Laboratory Products) coated by absorption with various human Ig at a concentration of 10 $\mu$g/ml. After coating, the plates were washed with PBS-5% FCS. To the coated wells, 25 $\mu$l of test culture samples were added. The plates were then incubated overnight at 4° C. and washed 4 times with PBS-5% FCS, after which $^{125}$I-labeled goat anti-mouse $\kappa$ was added. The plates were incubated for at least another 4 hr and washed. The wells were cut out with a hot wire device and counted in a gamma counter.

USE OF ANTIBODY TO MONITOR MALIGNANCY

The immunofluorescent staining technique used in this monitoring was as follows:

Reagents. Biotinylated IgM antibody was prepared by modification of the method described by Heitzmann and Richards (1975) *PNAS* 71: 3537. Partially purified antibodies at a concentration of 0.5 to 1 mg/ml were dialyzed against 0.1M NaHCO$_3$, pH 8.6. Biotin succinimide ester (Biosearch, San Rafael, CA) was dissolved in DMSO just before use at 1.0 mg/ml. To a 1-ml protein solution, 120 $\mu$l of biotin ester solution was added, and these were mixed and left at room temperature for 4 hr. The biotinylated antibody was dialyzed against PBS with 0.02% sodium azide overnight. Rhodamine-avidin and fluorescein-avidin were from Vector Laboratories, Burlingame, CA.

Method. PBL isolated by Ficoll (Pharmacia Fine Chemicals) Hypaque (Winthrop Laboratories, New York) sedimentation (Boyum (1968) *Scand. J. Clin. Lab.*

*Invest.* 21: 77) were washed with PBS, resuspended in RPMI 1640 medium containing 15% FCS, and cultured overnight at 37° C. in 5% $CO_2$ to remove cytophilic Ig. Cells stored in liquid $N_2$ were washed in RPMI 1640, and live cells were separated by Ficoll-Hypaque sedimentation. Cells were then suspended in 2% BSA, 0.02% sodium azide, at a concentration of $2 \times 10^7$/ml and 0.1 ml were incubated with an equal volume of biotinylated antibody for 20 min at room temperature. Cells were then washed twice with the BSA-azide solution and were incubated in a similar manner with the 2nd stage reagent, either rhodamine-avidin or fluorescein-avidin. After washing as above, the cells were layered on glass slides, covered with glass coverslips, and sealed with nail polish for viewing with a fluorescence microscope. Alternatively, the stained cells were fixed in 1% formaldehyde in PBS and analyzed on the FACS within 48 hr.

The monoclonal anti-$Id^{Ka}$ was used to stain PBL isolated from patient Ka and from 4 normal donors. Biotinylated monoclonal anti-$Id^{Ka}$ was used as a 1st stage, with rhodamine or fluorescein-avidin as the 2nd stage. PBL isolated from normal donors did not stain with the monoclonal anti-$Id^{Ka}$ antibody, whereas the percentage of Ka PBL stained correlated with the patient's clinical condition. The percentage of $Id^{Ka}+$ cells varied from a high of 75% of total mononuclear cells, taken when the disease was rapidly progressing clinically, to a low of 1% to 3% when the disease was in partial remission after chemotherapy.

Moreover, the patient's serum was analyzed for the amount of free circulating $Id^{Ka}$-Ig. The concentration of this protein was defined by RIA using a standard solution of purified $Id^{Ka}$-Ig as reference. The concentration of circulating $Id^{Ka}$-Ig in the patient's sera correlated well with the number of $Id^{Ka}+$ cells and with the patient's clinical condition. The lowest concentration of $Id^{Ka}$-Ig was found during apparent remissions, and the highest concentrations occurred when the disease was most active and apparent clinically.

USE OF THE ANTIBODY TO TREAT MALIGNANCY

Immunofluorescence Staining. For direct immunofluorescence staining, $1 \times 10^6$ cells were incubated with 100 µl (1 mg) of fluoresceinated antibodies for 20–30 minutes at 4° C. Indirect staining was performed in a similar manner using unlabeled first stage antibody. After washing, 100 µl of fluoresceinated goat anti-mouse IgG was added to the cells for 20–30 minutes at 4° C. Immunofluorescence staining of cells was analyzed using a FACS.

Frozen section immunoperoxidase staining of Ka tissue using the antibody was also performed.

Administration of Anti-Idiotype. The purified 4D6 antibody was given as a continuous six-hour infusion in 250 cc of normal saline containing 5% human albumin (400 mg antibody). Prior to each infusion the patient was given acetaminophen and diphenhydramine.

Assessment of Clinical Response. During the period of monoclonal antibody therapy, frequent complete blood counts, platelet counts, creatinine, electrolyte studies and hepatic and renal function tests were performed. Palpable cervicle, inguinal and axillary lymphadenopathy and hepatosplenomegaly were followed by physical examination. Abdominal roentgenograms were obtained to evaluate changes in opacified para-aortic and iliac lymphadenopthy seen on lymphangiogram.

Changes in tumor burden were estimated by measuring lymph node size on serially obtained abdominal films. Three lymph nodes on each side of the vertebral column, and one lymph node in the center, were used to calculate tumor volume by multiplying the larger diameter by the square of the smaller diameter of each lymph node. The sum of the volumes of these lymph nodes was then normalized to the value of the pre-treatment lymph node volume and was designated the tumor volume index.

Effect of Administration of Anti-Idiotype on Serum Idiotype Level. We anticipated that free circulating idiotype protein would be an obstacle to in vivo therapy with anti-idiotype. Moreover, the formation of immune complexes between idiotype and anti-idiotype might have been toxic. Since plasmapheresis was not able to reduce the idiotype level, the 4D6 antibody was given slowly on an intermittant schedule beginning with a low dose. Serum idiotype levels were unaffected by 1 or 5 mg of anti-idiotype but 15 mg caused a dramatic fall in idiotype level. Over the next five days, serum idiotype returned to approximtely two-thirds of the pre-treatment level. No toxicity was apparent and the patient experienced no side effects. Anti-idiotype was then administered in higher doses. Forty mg and 75 mg doses caused progressively greater decreases in serum idiotype. After 75 mg, idiotype dropped to undetectable levels for a short time but had reappeared just prior to a 150 mg dose. Subsequent to the 150 mg dose, idiotype was no longer detectable.

Detection of Monoclonal Anti-Idiotype in Serum During In Vivo Therapy. As would be expected, the detectability of anti-idiotype correlated with the disappearance of serum idiotype. After the 15 mg dose, circulating murine immunoglobulin was barely detectable and disappeared when idiotype levels rose. With the subsequent higher doses, serum anti-idiotype levels progressively rose with sharp increases seen after each dose. Serum anti-idiotype was detectable for over three weeks after the last doses of antibody. The serum levels of anti-idiotype were dose related as the bioavailability was greater for 150 mg > 135 mg > 85 mg. This relationship also depended on the absence of free idiotype.

Detection of 4D6 Anti-Idiotype in Lymph Node. After five doses of anti-idiotype, no measurable tumor response had been noted despite reduction in idiotype levels and appearance of circulating anti-idiotype. Despite these measurements it was important to determine if anti-idiotype could reach tissue sites such as lymph nodes. A repeat left cervical lymph node biopsy was performed two hours following the 150 mg dose of antibody. A cell suspension of this lymph node was stained with fluorescein-conjugated goat anti-mouse antibody to determine if murine antibody was present on the cells of the lymph node. Some murine antibody was present on the lymph node cells but these cells were not fully saturated since more intense staining could be obtained by incubation with additional 4D6 antibody in vivo. Thus, anti-idiotype was capable of penetrating and binding to cells within the lymph node, although the antigenic sites were not fully saturated at this time.

Tumor Response to anti-Idiotype Therapy. It should be emphasized that the patient received no therapy other than antibody during the period of this trial or in the preceding several weeks and that he had progressive tumor immediately prior to receiving the anti-idiotpe antibody. After the first two injections over the first week, the tumor volume index, as calculated from the lymphangiogram, actually increased slightly but the patient's fevers and sweats disappeared and his hemoglobin and platelet count rose. After the 40 mg dose, coincident with the marked fall in free idiotype and the persistence of anti-idiotype, a measurable tumor response began to occur. Gradually, over the ensuing weeks, the patient's enlarged lymph nodes regressed, his liver and spleen returned to normal size and tumors on his scalp disappeared. By four weeks, after eight doses of antibody, treatment was discontinued. The patient is currently in a complete remission over two years after the last antibody treatment. In order to explain the persisting tumor response outlasting the active period of therapy, we have looked at post-treatment patient serum for the presence of autologous anti-idiotype antibody, but none has been found.

Lack of Toxicity with Anti-Idiotype Therapy. There has been no acute or chronic toxicity from treatment with the anti-idiotype antibody. Specifically, there was no fever, chills, nausea, or allergy. Although this patient had impaired renal function prior to antibody therapy, there was no detectable further compromise of renal function as determined by serum creatinine and creatinine clearances. There was no detectable hepatic or hemotologic toxicity. Interestingly, the patient has made no antibody against the foreign mouse immunoglobulin.

Monoclonal anti-idiotype antibodies against the surface Igs of the B-cell tumors of five other patients were made using the general procedures described in the above example. The only difference in the antibody preparations was that whole hybridoma cells were used to immunize mice in some instances rather than isolated Ig from the hybridoma culture fluid. These antibodies and treatments are reported in the table below. The abbreviation used in the table are Id = idiotype
anti-Id = monoclonal anti-idiotype antibody
NLPD = nodular poorly differentiated lymphocytic lymphoma
PLL = prolymphocytic leukemia
DLPD = diffuse poorly differentiated lymphocytic lymphoma
LCL = large cell lymphoma
PR = partial remission
NR = no response
MR = minimal response

| Patient | Diagnosis | Isotype of Id | Cumulative Dose (mg anti-Id) | Isotype of Anti-Id | Serum Id (μg/ml) | Other Therapy | Clinical Response |
|---|---|---|---|---|---|---|---|
| FS | PLL | μκ | 1,530 | γ1 | 500 | — | PR |
| BL | NLPD | μκ | 2,101 | γ1 | 243 | — | NR |
| RD | DLPD-LCL | μλ | 5,000 | γ1 | 0.10 | Pre-Ab Radiotherapy | PR |
| BJ | NLPD | μκ | 2,492 | γ2b | 0.02 | Splenectomy | MR |
| CJ | NLPD | μκ | 3,079 | γ1 | 2.20 | Splenectoy | PR |

As indicated the treatment was effective for three out of five additional patients. Analysis of lymph node tissue from patient BL indicated that the antibody had not bound to the tumor cells. This failure to bind is believed to be attributable to the nature of the tumor and the high levels of circulating antigen.

Modifications of the above described modes of carrying out the invention that are obvious to those of skill in medicine, immunology, molecular biology and related field are intended to be within the scope of the following claims.

We claim:

1. An immunotherapeutic composition for treating a human patient for a B-cell malignancy comprising a monoclonal anti-idiotype IgG antibody against the surface Ig of the patient's B-cell tumor, said antibody being useful for treating the person bearing the tumor for the malignant condition associated with the tumor, and said antibody being useful in immunodiagnosis of the malignant condition associated with the tumor, combined with a pharmaceutically acceptable vehicle, the amount of said monoclonal anti-idiotype antibody in the composition being sufficient to induce a B-cell tumor elimination response in said patient.

2. The immunotherapeutic composition of claim 1 wherein the B-cell tumor is a substantially non Ig-secreting B-cell tumor.

3. The immunotherapeutic composition of claim 1 wherein said amount is in the range of about 10 mg to about 5 g.

4. The immunotherapeutic composition of claim 1 wherein the monoclonal anti-idiotype antibody is a murine monoclonal anti-idiotype antibody.

* * * * *